(12) United States Patent
Arnett

(10) Patent No.: US 11,696,597 B2
(45) Date of Patent: Jul. 11, 2023

(54) BOWL FOR EVAPORATION OF A SUBSTANCE FOR INHALATION

(71) Applicant: Adapt Tech, LLC, Reno, NV (US)

(72) Inventor: Casey Arnett, Dayton, NV (US)

(73) Assignee: Adapt Tech, LLC, Reno, NV (US)

( * ) Notice: Subject to any disclaimer, the term of this patent is extended or adjusted under 35 U.S.C. 154(b) by 780 days.

(21) Appl. No.: 16/596,023

(22) Filed: Oct. 8, 2019

(65) Prior Publication Data

US 2020/0120979 A1    Apr. 23, 2020

Related U.S. Application Data

(60) Provisional application No. 62/740,064, filed on Oct. 2, 2018.

(51) Int. Cl.
| | |
|---|---|
| *A24F 5/00* | (2006.01) |
| *A24F 40/40* | (2020.01) |
| *A61M 11/04* | (2006.01) |
| *A24F 1/32* | (2006.01) |
| *A24F 42/00* | (2020.01) |

(52) U.S. Cl.
CPC .......... *A24F 40/40* (2020.01); *A24F 1/32* (2013.01); *A24F 5/00* (2013.01); *A24F 42/00* (2020.01); *A61M 11/041* (2013.01)

(58) Field of Classification Search
CPC ........................................ A24F 1/32
See application file for complete search history.

(56) References Cited

U.S. PATENT DOCUMENTS

| | | | |
|---|---|---|---|
| 2014/0251355 A1* | 9/2014 | Tracey ................. | A24F 1/30 131/328 |
| 2015/0307406 A1* | 10/2015 | Pujol .................. | C04B 41/5007 264/669 |

* cited by examiner

*Primary Examiner* — Eric Yaary
(74) *Attorney, Agent, or Firm* — Goodman Law Center, P.C.

(57) ABSTRACT

A bowl for evaporation of a substance for inhalation comprises a cylindrical wall attached to a base. The bowl is made of a colorless single-crystal material selected from the group consisting of: alumina, magnesium-alumina spinel, yttrium-aluminum garnet, and cubic zirconium oxide. The bowl can have any desired color by doping the colorless single-crystal material by a transition metal. The transition metal is selected from a group consisting of: titanium, vanadium, chromium, iron and cobalt. The substance for evaporation can be positioned inside the bowl. In one embodiment, the bowl comprises a tapered cylindrical wall attached to a base. The tapered cylindrical wall can preferably be in shape of a truncated cone to which the base is attached.

9 Claims, 3 Drawing Sheets

BOWL FOR EVAPORATION OF A SUBSTANCE FOR INHALATION

TECHNICAL FIELD OF THE DISCLOSURE

The present disclosure relates generally to inhalation devices, and more particularly to an inhalation bowl for inhalation and evaporation of a substance.

DESCRIPTION OF THE RELATED ART

Inhalation devices have been widely utilized in medical fields for treating diseases and also find its application in satisfying human needs related to smoking. A wide variety of inhalation device acts as an alternative source for injections and capsules, by allowing the medicines to be vaped directly into the body. Vaporization is a finest method of consuming the substance which limits the toxins entering the airways. Generally, inhalation is considered as a more effective method since the effects of the inhaled products/substances such as medicines, cannabis, marijuana and tobacco may be felt by the consumer within seconds than by providing a controlled prescribed amount.

Conventional smoking devices are bulky in configuration and difficult to clean. In several existing methods, smoking has been performed using various devices that involves the combustion of the substance by an internal heating element which produces smoke stream in a filtered or an unfiltered form. However, the output smoke stream produced during the process of combustion does not enhance the quality and characteristics of the smoke thereby the users lack enjoyment of smoking.

In order to overcome such issues, smoking devices were developed in which a layer of aluminum foil is wrapped inside the device and the perforations are placed in the aluminum. Once the substance is lit, the aluminum begins to heat and this heat is transferred through the perforations to the tobacco product within the device. However, the ashes produced fall through the holes in the aluminum, get mixed with the tobacco and changes the flavour. Moreover, the heat is produced on top of the tobacco, causing it to burn quickly resulting in a harsh smoke, and the heat often does not transfer to the tobacco on the bottom of the bowl. Also the structural characteristic of the device is not capable of being incorporated with another smoking device and cleaning the device is a challenging task.

Therefore, there is a need for a device which can resist any temperature and should be bio-compatible. Such a device would allow the substances that are not typically ever vaporized or smoked to be accessed via vaping. Moreover, such a device would be capable of connecting with a glass pipe, an electronic vaporizer, vaporizer pen, and a bong. Moreover, such a device would be designed in a manner that does not devitrify at the high temperatures. Such a device would be made of transparent colorless single-crystal material with high hardness capacity. Further, the device would produce smoke at a lower temperature with minimal combustion of the substance or sometimes no combustion of the substance. The present embodiment overcomes shortcomings in the field by accomplishing these critical objectives.

SUMMARY OF THE DISCLOSURE

To minimize the limitations found in the existing systems and methods, and to minimize other limitations that will be apparent upon the reading of the specifications, preferred embodiment of the present invention provides a bowl for evaporation of a substance for inhalation.

The bowl comprises a cylindrical wall attached to a base. The substance for evaporation can be positioned inside the bowl. The bowl is made of a colorless single-crystal material selected from the group consisting of: alumina, magnesium-alumina spinel, yttrium-aluminum garnet, and cubic zirconium oxide. The bowl can have any desired color by doping the colorless single-crystal material by a transition metal. The transition metal can be selected to have a desired color for the bowl. The transition metal is selected from a group consisting of: titanium, vanadium, chromium, iron and cobalt. The bowl of the present embodiment preferably has an outside diameter ranging from 10 millimeters to 30 millimeters and the height ranges from 10 millimeters to 30 millimeters. The wall thickness of the bowl can preferably be between 0.5 millimeters and 3 millimeters and the thickness of the base can be between 0.5 millimeters and 5 millimeters. The diameter of the base can be between 12 millimeters and 256 millimeters.

In one embodiment, the bowl comprises a tapered cylindrical wall attached to a base. The tapered cylindrical wall can preferably be in shape of a truncated cone to which the base is attached.

A first objective of the present embodiment is to provide a bowl for smoking that provides better tasting and healthier vapor for smoking products like cannabis/marijuana and tobacco.

A second objective of the present embodiment is to provide a bowl in which the products can be smoked at a lower temperature that allows vapor to be withdrawn from the substance with minimal combustion of the products or sometimes no combustion of the products.

A third objective of the present embodiment is to provide a bowl that is bio-compatible with organic materials and conserves vaping material.

A fourth objective of the present embodiment is to provide a bowl that has hardness greater than 8.0 on Mohs scale and does not devitrify upon heating.

Another objective of the present embodiment is to provide a bowl that allows substances, including many medicinal substances, which are not typically ever vaporized or smoked to be accessed via vaping.

Yet another objective of the present embodiment is to provide a bowl that requires less heat as compared to quartz for proper vaporization.

Still another objective of the present embodiment is to provide a bowl that can be used with any oil or matter that is safe to consume and can be used with a glass pipe, an electronic vaporizer/vaporizer pen, a bong, etc.

These and other advantages and features of the present invention are described with specificity so as to make the present invention understandable to one of ordinary skill in the art.

BRIEF DESCRIPTION OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention, thus the drawings are generalized in form in the interest of clarity and conciseness.

DETAILED DESCRIPTION OF THE DRAWINGS

In the following discussion that addresses a number of embodiments and applications of the present invention, reference is made to the accompanying drawings that form a part hereof, and in which is shown by way of illustration specific embodiments in which the invention may be practiced. It is to be understood that other embodiments may be utilized and changes may be made without departing from the scope of the present invention.

Various inventive features are described below that can each be used independently of one another or in combination with other features. However, any single inventive feature may not address any of the problems discussed above or only address one of the problems discussed above. Further, one or more of the problems discussed above may not be fully addressed by any of the features described below.

As used herein, the singular forms "a", "an" and "the" include plural referents unless the context clearly dictates otherwise. "And" as used herein is interchangeably used with "or" unless expressly stated otherwise. As used herein, the term 'about" means+/−5% of the recited parameter. All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "wherein", "whereas", "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

Figure 1:
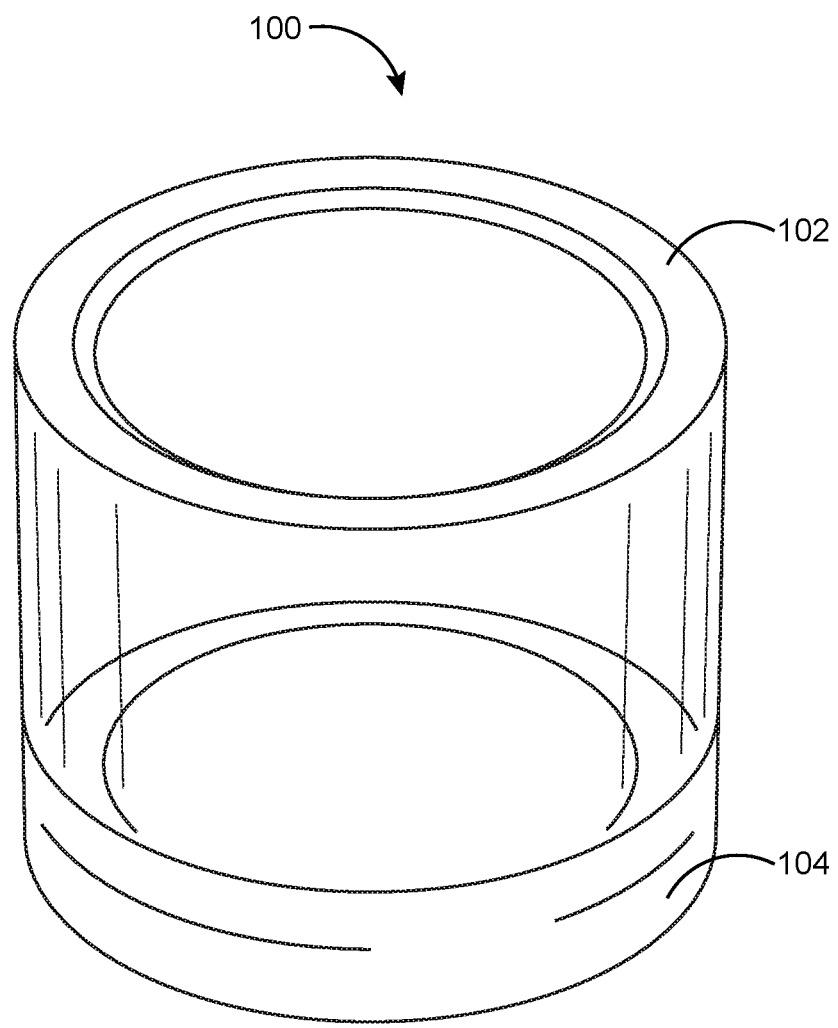
FIG. 1 illustrates a top perspective view of a bowl for evaporation of a substance for inhalation in accordance with the preferred embodiment of the present invention.
Figure 2:
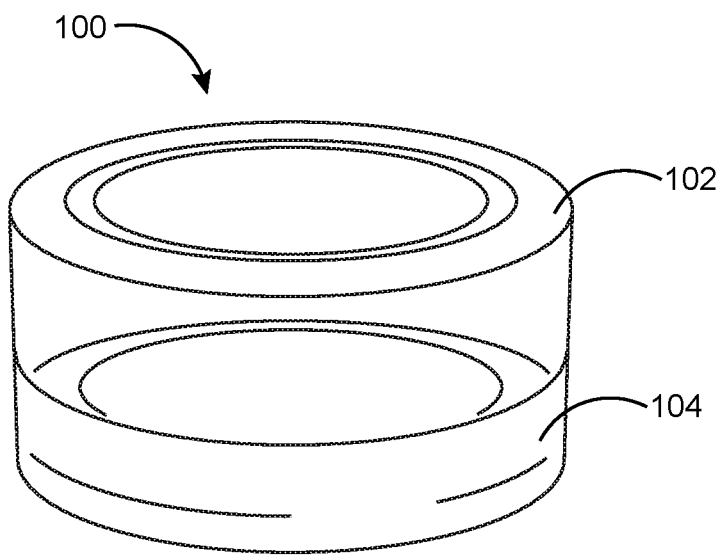
FIG. 2 illustrates a top perspective view of the bowl for evaporation of the substance for inhalation in accordance with one embodiment of the present invention.
Figure 3:
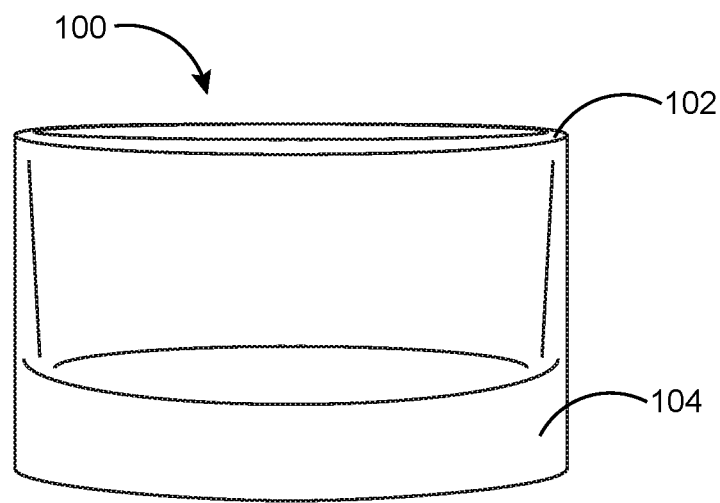
FIG. 3 illustrates a side perspective view of the bowl for evaporation of the substance for inhalation in accordance with one embodiment of the present invention.

Referring to FIGS. 1, 2 and 3, perspective views of a bowl 100 for evaporation of a substance for inhalation are illustrated. The bowl 100 of the present embodiment is utilized for evaporation of the substance, such as, for example, tobacco or marijuana. The substance can also include any medicinal substances that can be vaped as an alternative to injections or pills. The bowl 100 comprises a cylindrical wall 102 attached to a base 104. The substance for evaporation can be positioned inside the bowl 100. The bowl 100 is made of a colorless single-crystal material selected from the group consisting of: alumina, magnesium-alumina spinel, yttrium-aluminum garnet, and cubic zirconium oxide. The bowl 100 of the present embodiment preferably has an outside diameter ranging from 10 millimeters to 30 millimeters and the height ranges from 10 millimeters to 30 millimeters. The thickness of the wall 102 can preferably be between 0.5 millimeters and 3 millimeters and the thickness of the base 104 can be between 0.5 millimeters and 5 millimeters. The diameter of the base 104 can be between 12 millimeters and 256 millimeters.

In one embodiment, the bowl 100 can have any desired color by doping the colorless single-crystal material by a transition metal. The transition metal can be selected to have a desired color for the bowl 100. The transition metal is selected from a group consisting of: titanium, vanadium, chromium, iron and cobalt.

Figure 4:
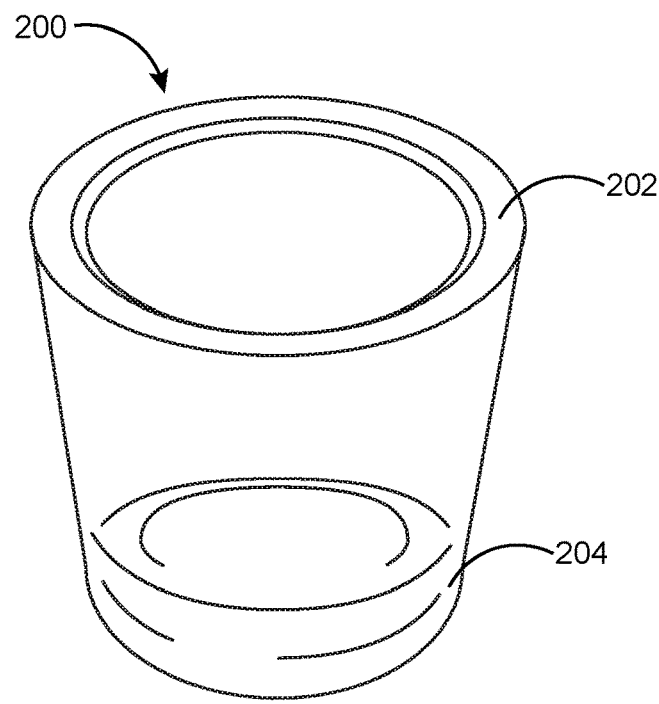
FIG. 4 illustrates a top perspective view of a bowl for evaporation of the substance for inhalation in accordance with an alternate embodiment of the present invention.
Figure 5:
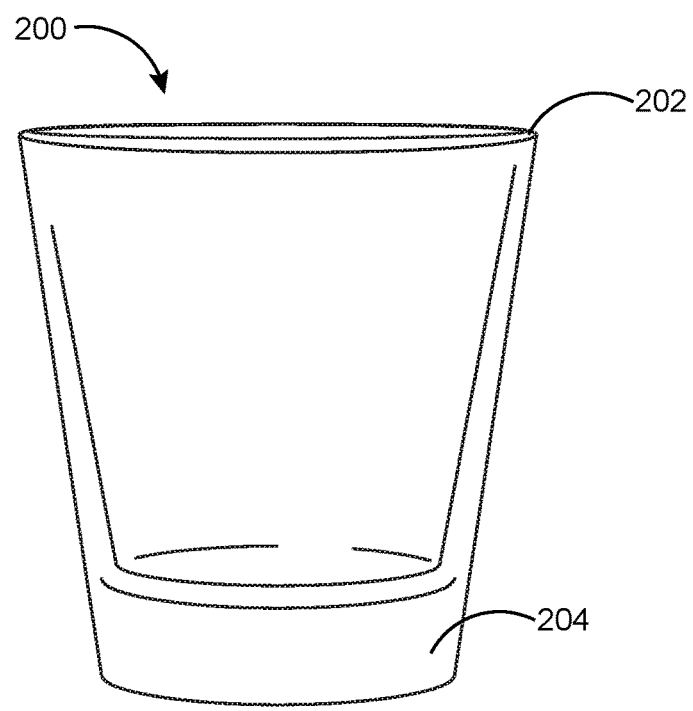
FIG. 5 illustrates a side perspective view of the bowl for evaporation of the substance for inhalation in accordance with the alternate embodiment of the present invention.

FIGS. 4 and 5 illustrate top perspective view and side perspective view respectively of a bowl 200 for evaporation of the substance for inhalation in accordance with an alternate embodiment of the present invention. This embodiment of the bowl 200 comprises a tapered cylindrical wall 202 attached to a base 204. The tapered cylindrical wall 202 can preferably be in shape of a truncated cone to which the base 204 is attached.

The bowl 100 of the present embodiment can be used for smoking and provides better tasting and healthier vapor for smoking products like cannabis/marijuana and tobacco. Utilizing the bowl 100 of the present embodiment, the products can be smoked at a lower temperature which allows vapor to be withdrawn from the substance with minimal combustion of the products or sometimes no combustion of the products. The bowl 100 has hardness greater than 8.0 on Mohs scale and does not devitrify upon heating. The bowl 100 is bio-compatible with organic materials and conserves vaping material. The bowl 100 requires less heat as compared to quartz for proper vaporization and can hold more heat.

The bowl 100 of the present embodiment further allows substances, including many medicinal substances, which are not typically ever vaporized or smoked to be accessed via vaping. For instance, lavender could be vaped. This embodiment also allows some medicines to be vaped as an alternative to injections or pills. The bowl 100 can be used with any oil or matter that is safe to consume. Further the bowl 100 of the present embodiment can be used with a glass pipe, an electronic vaporizer/vaporizer pen, a bong, etc.

The foregoing description of the preferred embodiment of the present invention has been presented for the purpose of illustration and description. It is not intended to be exhaustive or to limit the invention to the precise form disclosed. Many modifications and variations are possible in light of the above teachings. It is intended that the scope of the present invention not be limited by this detailed description, but by the claims and the equivalents to the claims appended hereto.

What is claimed is:

1. A bowl for the evaporation and inhalation of a substance, wherein:
   a. the bowl has a shape selected from the group consisting of a cylinder and a truncated cone;
   b. the bowl is made out of a colorless single-crystal material selected from the group consisting of magnesium-alumina spinel and yttrium-aluminum garnet; and
   c. the bowl enables substances not typically vaporized or smoked to be vaped.

2. The bowl of claim 1, wherein the colorless single-crystal material is doped by a transition metal, the transition metal being selected to cause the bowl to have a desired color.

3. The bowl of claim 2, wherein the transition metal comprises titanium.

4. The bowl of claim 2, wherein the transition metal comprises vanadium.

5. The bowl of claim 2, wherein the transition metal comprises chromium.

6. The bowl of claim 2, wherein the transition metal comprises iron.

7. The bowl of claim 2, wherein the transition metal comprises cobalt.

8. The bowl of claim 1, wherein the bowl has a shape of a truncated cone.

9. The bowl of claim 1, wherein the bowl enables medicinal substances to be vaped.

\* \* \* \* \*